US009658440B2

(12) United States Patent
Henneberg

(10) Patent No.: US 9,658,440 B2
(45) Date of Patent: May 23, 2017

(54) OPTICAL PROBE FOR MEASURING LIGHT SIGNALS IN VIVO

(75) Inventor: Morten Henneberg, Odense M (DK)

(73) Assignee: RSP SYSTEMS A/S, Odense S (DK)

( * ) Notice: Subject to any disclaimer, the term of this patent is extended or adjusted under 35 U.S.C. 154(b) by 1030 days.

(21) Appl. No.: 13/255,675

(22) PCT Filed: Mar. 12, 2009

(86) PCT No.: PCT/DK2009/000064
§ 371 (c)(1),
(2), (4) Date: Nov. 4, 2011

(87) PCT Pub. No.: WO2010/102621
PCT Pub. Date: Sep. 16, 2010

(65) Prior Publication Data
US 2012/0044484 A1 Feb. 23, 2012

(51) Int. Cl.
*A61B 5/00* (2006.01)
*G02B 21/00* (2006.01)
(Continued)

(52) U.S. Cl.
CPC ........ *G02B 21/0096* (2013.01); *A61B 5/0059* (2013.01); *A61B 5/0068* (2013.01);
(Continued)

(58) Field of Classification Search
CPC .......... A61B 2562/0242; A61B 5/0059; A61B 5/0068; A61B 5/145; A61B 5/1455;
(Continued)

(56) References Cited

U.S. PATENT DOCUMENTS

| 5,112,127 A | 5/1992 | Carrabba et al. |
| 5,842,995 A | 12/1998 | Mahadevan-Jansen et al. |

(Continued)

FOREIGN PATENT DOCUMENTS

| CN | 101213428 | 7/2008 |
| JP | 4-66873 | 3/1992 |

(Continued)

OTHER PUBLICATIONS

International Search Report mailed Apr. 12, 2009 for corresponding International Patent Application No. PCT/DK2009/000064.
(Continued)

*Primary Examiner* — Ruth S Smith
(74) *Attorney, Agent, or Firm* — Pillsbury Winthrop Shaw Pittman LLP

(57) ABSTRACT

An optical probe for measuring light signals includes a first optical fiber guiding incoming light, a lens focusing incoming light towards a sample and collecting altered light from the sample, a second optical fiber guiding altered light, a light logging device measuring intensity fluctuations in the incoming light, wherein the light logging device is positioned after the first optical fiber, whereby the light logging device receives a part of the incoming light from the first fiber. The optical probe is normally applied for measuring light signals in vivo, and finds its primary applications within the field of optical spectroscopic measurements, where the light signals measured by the probe are applied in combination with an apparatus wherein light signals are analyzed against its spectral components for instance in Raman, fluorescence, phosphorescence absorption, diffusion and transmission studies.

14 Claims, 4 Drawing Sheets

(51) Int. Cl.

| | |
|---|---|
| *A61B 5/145* | (2006.01) |
| *A61B 5/1455* | (2006.01) |
| *G01N 21/31* | (2006.01) |
| *G01N 21/64* | (2006.01) |
| *G02B 21/08* | (2006.01) |
| *A61B 5/1495* | (2006.01) |

(52) U.S. Cl.
CPC ............ *A61B 5/145* (2013.01); *A61B 5/1455* (2013.01); *G01N 21/31* (2013.01); *G01N 21/64* (2013.01); *G02B 21/082* (2013.01); *A61B 5/1495* (2013.01); *A61B 2562/0242* (2013.01)

(58) Field of Classification Search
CPC ...... A61B 5/1495; G01N 21/31; G01N 21/64; G02B 21/0096; G02B 21/082
See application file for complete search history.

(56) References Cited

U.S. PATENT DOCUMENTS

| | | | | |
|---|---|---|---|---|
| 5,882,301 | A  * | 3/1999 | Yoshida | 600/318 |
| 6,140,651 | A  * | 10/2000 | Justus et al. | 250/390.11 |
| 6,167,290 | A | 12/2000 | Yang et al. | |
| 6,291,132 | B1 * | 9/2001 | Glushko et al. | 430/270.15 |
| 2004/0019283 | A1 * | 1/2004 | Lambert et al. | 600/476 |
| 2005/0036147 | A1 | 2/2005 | Sterling et al. | |
| 2007/0091325 | A1 * | 4/2007 | Nikoonahad | 356/625 |
| 2010/0014076 | A1 | 1/2010 | Henneberg et al. | |
| 2010/0179436 | A1 * | 7/2010 | Sarfaty et al. | 600/476 |

FOREIGN PATENT DOCUMENTS

| | | |
|---|---|---|
| JP | 9-321335 | 12/1997 |
| WO | 99/27848 | 6/1999 |
| WO | 2004/055473 | 7/2004 |
| WO | 2004/082474 | 9/2004 |
| WO | 2005/012553 | 2/2005 |
| WO | 2006/059226 | 6/2006 |
| WO | 2007/014173 | 2/2007 |

OTHER PUBLICATIONS

International Preliminary Report on Patentability dated Jul. 1, 2011 for corresponding International Patent Application No. PCT/DK2009/000064.

Urs Utzinger et al., "Fiber optic probes for biomedical optical spectroscopy," Journal of Biomedical Optics, vol. 8, No. 1, pp. 121-147 (Jan. 2003).

P.J. Caspers et al., "Combined In Vivo Confocal Raman Spectroscopy and Confocal Microscopy of Human Skin," Biophysical Journal, vol. 85, pp. 572-580 (Jul. 2003).

Chinese Office Action dated Jun. 26, 2013 in corresponding Chinese Patent Application No. 2009801580088.

Translation of Office Action mailed on Oct. 4, 2013 in counterpart Japanese Patent Appln. No. 2011-553283.

* cited by examiner

OPTICAL PROBE FOR MEASURING LIGHT SIGNALS IN VIVO

CROSS REFERENCE TO RELATED APPLICATIONS

This application is the National Phase entry of PCT/DK2009/000064, filed Mar. 12, 2009. The content of this application is incorporated herein by reference in its entirety.

The invention relates to an optical probe for measuring light signals in vivo. It finds applications within the field of optical spectroscopic measurements, where the light signals measured by said probe are applied in combination with an apparatus wherein light signals are analyzed against its spectral components for instance in Raman, fluorescence, phosphorescence absorption, diffusion and transmission studies. The present invention especially relates to and finds application within the area of Raman Spectroscopy.

BACKGROUND

Spectroscopy is a method for obtaining information on a molecular scale by the use of light. This information can be related to the rotational, vibrational and/or electronic states of the molecules probed as well as dissociation energy and more. The rotational and/or vibrational spectrum of a given molecule is specific for that molecule. As a consequence, molecular spectra are often referred to as 'fingerprints' related to a specific molecule. Information related to in particular rotational, vibrational and/or electronic states of molecules can therefore be used to analyze a sample comprising a number of unknown molecular components, thereby obtaining knowledge about the molecular components in the sample.

The basis for a spectroscopic setup is a light source, e.g. a laser, which is used for illuminating a sample. The light from the light source (the incoming light) will interact with the sample, which often results in an alternation of the light which is transmitted through, emitted by, reflected by and/or scattered by the sample. By collecting the altered light and analyzing its spectral distribution, information about the interaction between the incoming light and the molecular sample can be obtained; hence information about the molecular components can be obtained.

The spectral distribution is typically measured by using a spectrometer. A spectrometer is an optical apparatus that works by separating the light beam directed into the optical apparatus into different frequency components and subsequently measures the intensity of these components by using a CCD detector, a CCD array, photodiode or such.

The altered light reflecting interactions between the incoming light and the molecular sample can normally be characterized as either emission or scattering. Emission signals have relatively broad spectral profiles as compared to scattering light signals, which normally display quite narrow spectral lines. One process is often dominating over the other, but both processes can and will most often occur simultaneously. The intensity of the emitted light vs. the intensity of the scattered light depends among others on the frequency and the power of the incoming light, the intensity of the incoming light at the measuring point in the sample, and the molecular components in the sample.

Emission describes the process when a molecule absorbs light from a light source, e.g. a laser, and afterwards emits light again. The emitted light is normally characterized by having a different spectral distribution compared to the incoming light, and will have a relatively broad spectral distribution reflecting the different rotational and/or vibrational states of the electronic state(s) in the molecules. The majority of emission processes can be characterized as either fluorescence or phosphorescence, where the spin of the electronic states in the molecule involved in absorption and emission of light is the same in the fluorescence process but different in the phosphorescence process. In general, fluorescence can be characterized as a spectroscopically allowed process, whereas phosphorescence is a spectroscopically forbidden process based on the conversion and the alteration of the electronic state spins, respectively. The intensity of phosphorescence signals is consequently normally much weaker than fluorescence signals.

Scattered light can be classified as being either elastic or inelastic and is characterized by being spectroscopically very narrow signals. Elastic scattering is referred to as Rayleigh scattering, in which there is no frequency shift, i.e. Rayleigh scattering has the same frequency as that of the incoming light.

The most commonly known example of inelastic scattering is Raman scattering, in which there is an energy interchanging between the molecule and the photons of the incoming light. The frequencies, i.e. the spectral distribution of the Raman scattered light, will be different from that of the incoming light and uniquely reflect the specific vibrational levels of the molecule; hence it is a fingerprint spectrum. This can be used for identification of the molecular composition of the substance probed and/or the concentration of the specific molecules in the substance.

Raman scattering is a relatively weak process compared to Rayleigh scattering and fluorescence. Reduction of contributions from these other processes is thus desirable when collecting Raman scattered light. In addition, the intensity of the Raman scattered light depends strongly on the frequency and the intensity of the incoming light. It is therefore essential to monitor power fluctuations in the incoming light if one is to receive reliable information about the distribution of molecular components in different samples and/or sample spots based on an analysis of the collected Raman scattered light. The same is true if the analysis of the molecular components in a sample and/or different sample spots is based on emission spectra.

In order to collect the altered light and direct it into an apparatus, e.g. a spectrometer, for the subsequent analysis, an optical probe is required. Such normally comprises a combination of different optical components, like lenses, mirrors and fibers, and is characterized by having a leg for the incoming light and a leg for the altered light.

A microscope can be used as an optical probe or incorporated as part of one. A microscope objective in the microscope focuses the incoming light onto a sample and collects the altered light. Alternatively, a second microscope objective can be employed for collecting the altered light. A microscope-based optical probe is not a movable object, and the samples studied with such a probe consequently need to be inserted into the microscope or placed on top of it depending on the direction of the incoming light and the position of the microscope objective. Samples collected in vitro and placed on e.g. cover slips or other types of thin plates are preferable and easy to work with in a microscope. Measurements of e.g. blood sugar levels in a patient can be performed when provided with a blood sample from the patient. However, it requires an educated person to obtain a blood sample from a patient and the process if self can be somewhat unpleasant for the patient. An alternative to this in vitro method is for the patient to insert his/her arm directly under or above the microscope objective in the microscope for an in vivo measurement of the blood sugar level. Unfortunately, this is cumbersome if not impossible with most microscopes.

An optical probe employing not the entire microscope but only microscope objective(s) mounted separately on e.g. a table allows for a larger accessibility between probe and sample. In vivo measurements of blood sugar levels in a patient become more convenient as the patient's arm or finger can be placed in front of the microscope objective(s) without much difficulty. However, if the chosen sample is a leg, it might prove more difficult to place it appropriately in front of the microscope objective(s). Furthermore, in vivo diagnostics of skin abnormalities in the cervix, i.e. examination of the potential risk of cervical cancer, are impossible to perform using a microscope objective mounted on a table or such.

Consequently, there is a need for a movable and flexible optical probe in order to measure optical signals in vivo. One way to solve this is to employ fibers for guiding the light into and/or away from the probe. Different examples of such can be found in the literature.

The optical probe described in U.S. Pat. No. 5,842,995 finds its primary application within the field of diagnostic of skin abnormalities as a result of e.g. cancer, and is based on fibers both for directing the incoming light onto the sample and for collecting the altered light from the sample. The incoming light passes through a broadband filter before it reaches the sample and the altered light from the sample is collected in a multicore fiber. The leg for the incoming light and the leg for collecting the altered light are aligned co-parallelly and share no optical components.

The optical probe found in U.S. Pat. No. 5,112,227 comprises a leg for the incoming light and a leg for collecting the altered light, where the two legs are aligned co-parallelly, and share the same lens for focusing the light into the sample and for collecting the altered light from the sample. An optical filter placed at a 45° angle before the lens, allows the incoming light to pass through and reflects the altered light from the sample, thereby separating the two optical legs.

In *Journal of Biomedical Optics* vol. 8, page 221-147 (2003) (referred to as *J. Bio. Opt.* from hereon), several different optical probes are described. The probes are primarily multi-core fiber probes without optical focusing means. The majority of the probes have a leg for the incoming light and a leg for collecting the altered light, where the two legs are aligned co-parallelly. U.S. Pat. No. 5,842,995, U.S. Pat. No. 5,112,227, and *J. Bio. Opt.* all describe flexible and movable optical probes. However, none of these probes account accurately for intensity variations in the incoming light.

The process of coupling laser light into a fiber is quite sensitive to the angle at which the laser light is focused into the fiber and the distance between the focus point of the lens, which focuses the laser into the fiber, and the fiber itself. Variations in the intensity of light coming out a fiber will vary as a result of the efficiency by which the laser light is coupled into the fiber. As a consequence, alternations in the intensity of the altered light from the sample will both reflect intensity variations in the incoming light and variations within the sample. Means for accurate detection of the intensity of the incoming light directly before the light is focused into the sample, are thus crucial if one wants to obtain an intensity variation pattern solely reflecting sample variations. Common for the optical probes described in U.S. Pat. No. 5,842,995, U.S. Pat. No. 5,112,227, and *J. Bio. Opt.*, is that none of them provide this.

In addition, when the incoming light is focused into the sample, the altered light will not only come from the focus spot of the incoming light, but also from the cone-shaped area both above and below the focus spot. Hence, the light signals measurable with the probes described in U.S. Pat. No. 5,842,995, U.S. Pat. No. 5,112,227, and *J. Bio. Opt.* will contain additional and often unwanted contributions from sample areas outside the focus spot. Confocal imaging employing apertures of some kind is one way to obtain precise information on the spectral components at the focus spot without contributions from the sample above and below this point.

The article found in *Biophysical Journal* vol. 85, page 572-580 (2003) describes an optical probe for measuring primarily water profiles within the skin in vivo. The leg for collecting the altered light from the sample comprises an optical fiber, where coupling of the light into the fiber provides means for collecting a confocal image due to the small aperture-like diameter of the fiber. The probe comprises two lasers which can provide the incoming light and which are both focused onto the skin by a microscope objective. As the two lines for the incoming light do not use fibers, the microscope objective needs to be mounted at a fixed position. As a consequence, there is a reduced accessibility of sample spots, i.e. skin areas, which can be examined using this probing setup. Among others, diagnostics of skin abnormalities in the cervix in vivo, i.e. examination of the potential risk of cervical cancer, is excluded with this optical probe.

An optical probe for measuring optical signals in vivo, which is flexible, portable and accurately accounts for both variations in the incoming light and unwanted light signals from outside the sample focus spot, is therefore needed.

OBJECT AND DESCRIPTION OF THE INVENTION

The object of the present invention is to solve the above described problems.

The invention relates to an optical probe for measuring light signals comprising a first optical fiber guiding incoming light, a lens focusing incoming light towards (i.e. into or onto) a sample and collecting altered light (e.g. scattered and/or emitted light) from said sample, a second optical fiber guiding altered light and a light logging device measuring intensity fluctuations in said incoming light, characterized in that said light logging device is positioned after said first optical fiber, whereby said light logging device receives a part of said incoming light from said first fiber.

Inside the optical probe, said light logging device will normally be positioned after a dichroic mirror, which allows a minor part of the incoming light to either pass through the dichroic mirror and onto said light logging device, or to be reflected by the dichroic mirror onto said light logging device.

Alternatively, a splitting device can be positioned between said first fiber and said dichroic mirror, where said splitting device reflects a minor part of the incoming light onto said light logging device.

One advantage with using a light logging device is that it allows for a precise measuring of the variations in the intensity of the incoming light at all time. This ensures that variations in the intensity of the altered light only reflect sample variations and not variations in the incoming light.

In an embodiment of the invention, said lens focusing incoming light towards said sample is arranged at the surface of said optical probe such that said lens is in direct contact with said sample (213) during measuring.

An advantage with having the lens in direct contact with the sample during measurement is that the sample penetration depth, and thereby the distance from the optical probe to the sample focus point, is exactly known, as it is defined by the focal length of the lens.

In another embodiment of the invention, said optical probe further comprises a window, where said window is positioned between said lens and said sample, such that said window is in direct contact with said sample during measuring, and where the thickness of said window is smaller than the focal length of said lens.

An advantage with inserting a window between the lens and the sample is that it can provide an easier cleaning of the optical probe, if a fragile lens sensitive to cleaning is used.

Another advantage with inserting a window between the lens and the sample is that the penetration depth can be varied depending on the thickness of the window. The probe can thereby be applied for measuring skin abnormalities if the thickness of the applied window is comparable to focal length of the lens.

The optical probe according to the invention further comprises a dichroic mirror positioned after said first optical fiber, where said dichroic mirror reflects any percent between re_in=0 and 100 and transmits any percent between tr_in=0 and 100 of said incoming light, where re_in +tr_in=100 percent, and reflects any percent between re_se=0 and 100 and transmits any percent between tr_se=0 and 100 of said altered light, where re_se+tr_se=100 percent.

Said dichroic mirror is normally positioned at an angle of 45 degrees in relation to the propagating direction of said incoming light out of said first optical fiber.

In an embodiment of the invention, re_in ≥90 percent, tr_in ≤10 percent, re_se≤30 percent, tr_se≥70 percent, hence said dichroic mirror is reflecting the majority of the incoming light and transmitting the majority of the altered light.

In an embodiment where the majority of the incoming light is reflected by the dichroic mirror, said light logging device is positioned after said dichroic mirror, whereby said light logging device measures intensity fluctuations in said incoming light transmitted through said dichroic mirror.

An advantage with having the light logging device positioned directly after a dichroic mirror, which reflects the majority of the incoming light, is that it utilizes the minor part of the incoming light, which is transmitted by the dichroic mirror, and otherwise would be lost. There is consequently no need for any additional optical components to be inserted inside the optical probe in order to collect light for measuring of the fluctuations in the incoming light.

In an embodiment of the invention, re_in ≤10 percent, tr_in ≥90 percent, re_se≥70 percent, tr_se≤30 percent, hence said dichroic mirror is transmitting the majority of the incoming light and reflecting the majority of the altered light.

In an embodiment where the majority of the incoming light is transmitted by the dichroic mirror, said light logging device is positioned after said dichroic mirror, whereby said light logging device measures intensity fluctuations in said incoming light reflected of by said dichroic mirror.

An advantage with having the light logging device positioned at an angle directly after a dichroic mirror, which transmits the majority of the incoming light, is that it utilizes the minor part of the incoming light, which is reflected by the dichroic mirror, and otherwise would be lost. There is consequently no need for any additional optical components to be inserted inside the optical probe in order to collect light for measuring of the fluctuations in the incoming light.

In yet another embodiment where the majority of the incoming light is reflected by the dichroic mirror, a splitting device is positioned between said first optical fiber and said dichroic mirror, whereby said light logging device measures intensity fluctuations in said incoming light reflected by said splitting device and onto said light logging device.

A splitting device is an advantage if the dichroic mirror is either transmitting or reflecting nearly 100 percent of the incoming light, thereby not allowing a large enough part of the incoming light to be reflected or transmitted, respectively, onto the light logging device.

In one embodiment of the invention, the angle α between the direction (239) of light out of said first optical fiber (203) and the direction (241) of light entering said second optical fiber (227) is substantially α=90 degrees. The angle could also be α=80-100 degrees.

In one embodiment of the invention, said optical probe further comprises at least a first aperture where said first aperture only allows altered light from the focus point in said sample to enter said second fiber thereby ensuring a confocal image, and where said first aperture is positioned immediately in front of said second fiber. Said aperture can be a separate element. However, a narrow opening of said second fiber can equally well function as said aperture.

An advantage with using an optical aperture positioned before the second fiber is that the optical aperture works as a 3D depth filter eliminating optical signals generated outside the confocal area, i.e. the sample focus spot. The advantage with using a confocal optical probe is that the altered light entering the second fiber arises solely from interactions between the incoming light and the sample at the focus spot; hence contributions from the cone-like areas above and below the focus spot are eliminated.

In another embodiment of the invention, one or more apertures can additionally be employed to obtain a sharper 3D depth image. A second aperture is preferably positioned between the sample and the lens focusing the light into/onto the sample. This second aperture can be a separate element, but a narrow opening of the optical probe at the point where light is focused out/collected by the lens can equally well function as an aperture.

In one embodiment of the invention, said optical probe is applied for measuring optical signals in vivo. Alternatively, it could also be employed for measuring optical signals by immersing it into e.g. a blood sample thereby making the measurement in vitro.

Normally, the optical elements found inside the optical probe according to the present invention are enclosed by a cover. The optical probe can be moved around freely due to the use of flexible fibers for guiding light into and out of the optical probe.

A primary application of the optical probe is to measure blood sugar levels in a patient in vivo using different body areas such as an arm, a finger, a leg or similar. The probe can, however, also be used for measuring e.g. the level of haemoglobin, cholesterol, alcohol and/or drug in the blood or the temperature and/or variations of the temperature in the blood. Alternatively, the optical probe can be used for in vivo measurement of optical signals from skin layers, skin deformations and such e.g. found in the cervix when diagnosing the risk of cervical cancer.

A method for collecting optical signals from a sample comprising the steps of illuminating said sample with light from a light source by means of an optical probe, collecting altered light from said sample by means of said optical probe and analysing spectral components of said altered light from said sample is normally used for measuring optical signals from a sample using the optical probe according to the invention.

In one embodiment of the invention, said optical probe is applied in combination with an apparatus for analysing light signals against their spectral components in for instance Raman, fluorescence, phosphorescence absorption, diffusion and transmission.

DESCRIPTION OF PREFERRED EMBODIMENTS

Figure 1:
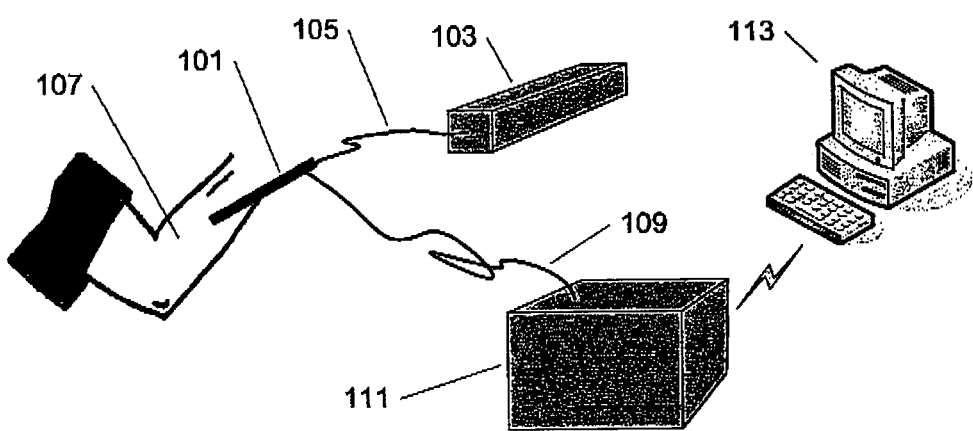
FIG. 1 shows an application of the optical probe.

FIG. 1 illustrates how the optical probe can be applied for measuring light signals in vivo. The optical probe 101 receives light from a light source 103 through a first fiber 105. In this embodiment of the invention, the light source 103 is a laser. The incoming light illuminates and interacts with the sample 107, where after the altered light altered from the sample is collected by the optical probe 101 and is guided via a second fiber 109 to a spectrometer 111 connected to a computer 113 for subsequent analysis of the spectral components.

In this embodiment of the invention, the sample is a patient's arm, but it could also be a finger or another body part. Likewise, the measurement is displayed as being carried out in vivo, but the optical probe 101 could also be employed for measuring optical signals by immersing it into e.g. a blood sample thereby making the measurement in vitro.

Normally, the optical elements found inside the optical probe 101 according to the present invention are enclosed by a cover, where the cover has at least one opening for the two fibers 105 and 109 and an opening for the light illuminating the sample. The latter opening is also used for collecting the altered light from the sample. The optical probe 101 can be moved around freely due to the use of flexible fibers for guiding light into and out of the optical probe.

A primary application of the optical probe 101 is to measure blood sugar levels in a patient in vivo using different body areas such as an arm, a finger, a leg or similar. The probe can, however, also be used for measuring e.g. the level of haemoglobin, cholesterol, alcohol and/or drug in the blood or the temperature and/or variations of the temperature in the blood. Alternatively, the optical probe can be used for in vivo measurement of optical signals from skin layers, skin deformations and such e.g. found in the cervix when diagnosing the risk of cervical cancer.

Figure 2:
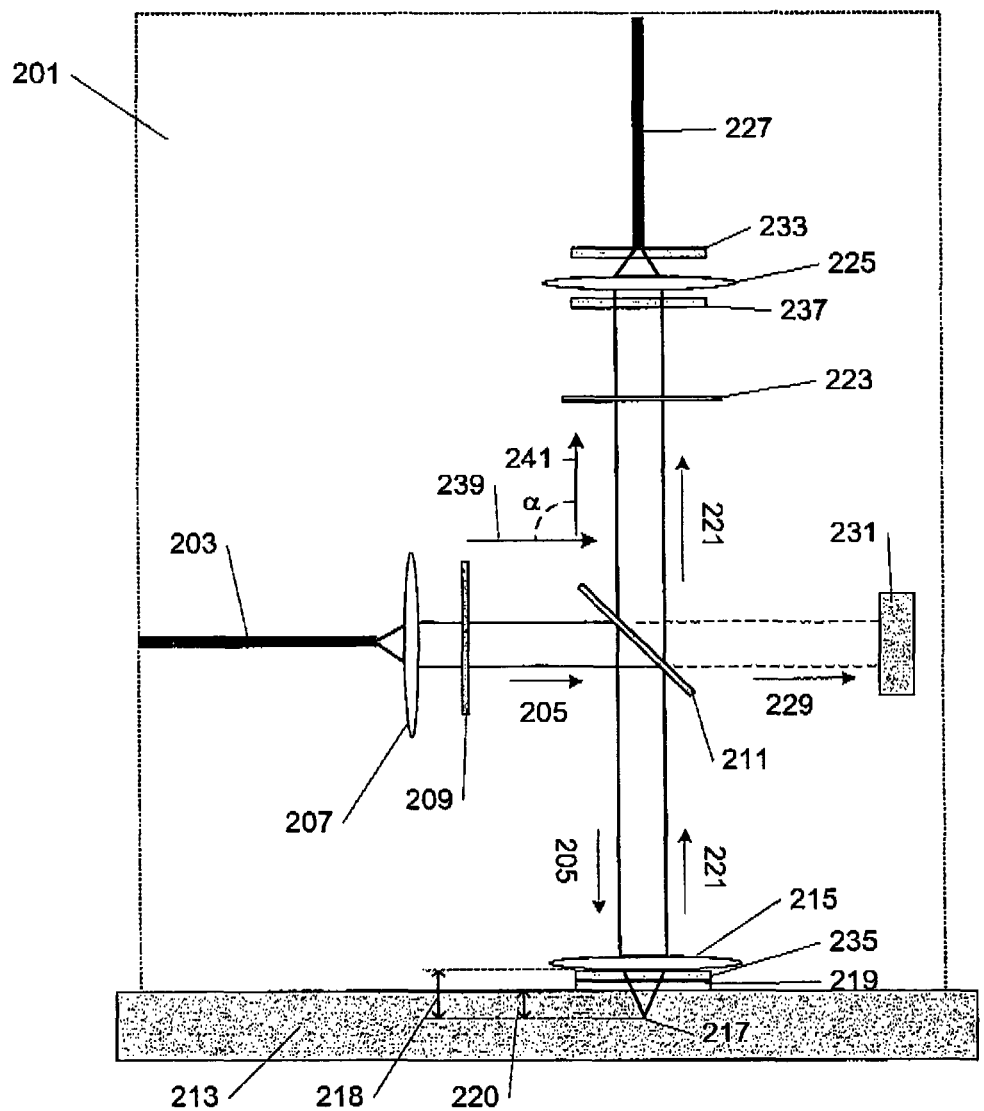
FIG. 2 shows a first embodiment of an optical probe according to the invention.

FIG. 2 shows a first embodiment of the optical probe 201 comprising a first optical fiber 203 for guiding light into the optical probe 201. According to this embodiment of the invention, the light source is normally a laser. Upon exiting the first fiber 203, the incoming light 205 is collimated using a first lens 207 and optically filtrated by passing through a first filter 209 blocking any percentage between 0 and 100 of frequencies outside the laser frequency. Blocking of frequencies outside the laser frequency ensures that e.g. Raman scattering generated inside the first fiber 203 is removed from the incoming light 205. The first filter 209 may also block any percentage between 0 and 100 of the laser frequency. This is an advantage if the intensity of the incoming light 205 is too high for the requirements of the sample. The first filter 209 is preferably a band-pass filter, a notch filter, an edge filter or such.

The optical probe 201 further comprises a dichroic mirror 211 that either reflects or transmits any percentage between 0 and 100 of the light, where the percentage of reflected and transmitted light is dependent on the coating on the dichroic mirror 211, the angle at which the light hits the dichroic mirror 211, and the frequency of the light. The dichroic mirror 211 can e.g. be coated such that it reflects the highest percent of the incoming light 205 when the dichroic mirror 211 is positioned at a given angle in relation to the direction of the incoming light 205. Changing the angle between the dichroic mirror 211 and the incoming light 205 will therefore reduce the percent of incoming light 205 reflected by the dichroic mirror 211.

In this embodiment of the invention, the majority of the incoming light 205 is reflected by the dichroic mirror 211 and focused inside a sample 213 by a second lens 215. The focus point 217 of the incoming light 205 is defined by the focal length 218 of the second lens 215. The second lens 215 is preferably convex, but could also be planar.

The dichroic mirror 211 is in the current embodiment positioned at an angle of 45° in relation to the propagating direction of the incoming light 205. The majority of the incoming light 205 is consequently reflected at a 90° angle. The dichroic mirror 211 could be positioned at an angle between 0-90° as well.

In one embodiment of the invention, the percent of the incoming light 205 which is reflected and transmitted by the dichroic mirror 211 is $re\_in \geq 90$ and $tr\_in \leq 10$, respectively, where $re\_in + tr\_in = 100$ percent.

In another embodiment of the invention, the percent of the incoming light 205 which is reflected and transmitted by the dichroic mirror 211 is $re\_in \geq 98$ and $tr\_in \leq 2$, respectively, where $re\_in + tr\_in = 100$ percent.

The optical probe 201 may further comprise a narrow window 219, which is positioned between the second lens 215 and the sample 213. The thickness of the window 219 is smaller than the focal length 218 of the second lens 215, i.e. smaller than the distance from the second lens 215 to the focus point 217 inside the sample 213. The window 219 can be applied for protecting the second lens 215 thereby enabling easy cleaning of the optical probe 201 after it has been in contact with the sample 213. Windows 219 of different thickness may also be applied thereby altering the sample penetration depth 220. Typical sample penetration depths 220 are in the range between ¹⁄₁₀-3 mm depending on the focal length 218 of the second lens 215 and the thickness of the window 219. Both shorter and longer penetrations depths 220 can also be obtained.

In another embodiment of the invention, there is no window 219, and the second lens 215 is in direct contact with the sample 213. Typical sample penetration depths 220 are in the range between ¹⁄₁₀-3 mm depending on the focal length 218 of the second lens 215. Both shorter and longer penetrations depths 220 can also be obtained, again reflecting the well defined focal length 218 of the second lens 215.

In addition to focusing the incoming light 205 into/onto the sample 213, the second lens 215 collimates the altered light 221 from the focus point 217 in the sample 213. In the current embodiment, the dichroic mirror 211 transmits the majority of the altered light 221, but reflects backscattering of the incoming light 205. This filters unwanted frequencies, i.e. the frequency of the back reflected incoming light 205, from the altered light 221, the latter generated as a result of interactions with the sample 213.

In one embodiment of the invention, the percent of the altered light 221 which is reflected and transmitted by the dichroic mirror 211 is re_se≤30 and tr_se≥70, respectively, where re_se+tr_se=100 percent.

In another embodiment of the invention, the percent of the altered light 221 which is reflected and transmitted by the dichroic mirror 211 is re_se≤10 and tr_se≥90, respectively, where re_se+tr_se=100 percent.

The altered light 221 is further optically filtrated by passing through a second filter 223 before the light is focused by a third lens 225 into a second fiber 227. The second filter 223 is preferably a band-pass filter, a notch filter, an edge filter or such and is characterized by transmitting any percentage between 0 and 100 of the altered light 221 collected by the second lens 215 and by blocking any percentage between 0 and 100 of frequencies close or equal to the frequency of the incoming light. This can e.g. insure that the percentage of unwanted Rayleigh scattering passing through the second filter 223 is neglectable at the same time as nearly all Raman light scattered from the sample 213 is allowed to pass through.

When measuring emission, such as fluorescence, it can be of interest to reduce the intensity of the light reaching a detection device, in order to avoid saturation and/or damage to the detection device. To achieve this, a second filter 223, which allows less than 100% of the emission to pass through, can be employed.

In this embodiment of the invention, the dichroic mirror 211 does not reflect all of the incoming laser light 205. Instead it allows a smaller fraction 229 of the light to be transmitted through the dichroic mirror 211 and onto a light logging device 231, which detects the intensity and/or power of the light 229 after passing through the dichroic mirror 211. The light logging device 231 can be a photodiode, a CCD detector, a thermal transistor or a fiber guiding to such a device, or similar.

One advantage with using a light logging device 231 is that it allows for a precise measurement of the variations in the intensity of the incoming light 205 at all time. This ensures that variations in the intensity of the altered light 221 only reflect sample variations and not variations in the incoming light.

Incorporating the light logging device 231 into the optical probe 201 and having it positioned after coupling the incoming light 205 out of the first fiber 203 is a clear advantage, since the process of coupling laser light into a fiber is quite sensitive to both the angle at which the laser light is focused into the fiber and the distance between the focus point of the lens, which focuses the laser into the fiber, and the fiber itself. Variations in the intensity of the light coming out of the fiber will thus vary as a result of the efficiency by which the laser light is coupled into the fiber. Using a light logging device positioned between the laser and the fiber as in the previously described patents/articles will therefore not give a precise measurement of the intensity variations of the light focused into the sample. Variations in the intensity of the altered light will not only reflect sample variations, but instead a combination of this and of the variations in the incoming light. This problem is solved by using the light logging setup as shown in this invention.

In addition to the above described optical elements, the optical probe 201 may also be equipped with at least a first optical aperture 233 positioned before the second fiber 227.

The first optical aperture 233 works as a 3D depth filter eliminating optical signals generated outside of the confocal area, i.e. the focus spot 217. The advantage with using a confocal optical probe is that the altered light 221 entering the second fiber 227 arises solely from interactions between the incoming light 205 and the sample 213 at the focus spot 217; hence contributions from the cone-like areas above and below the focus spot 217 are eliminated.

According to this first embodiment of the invention, the first aperture 233 is displayed as a separate element. However, a narrow opening of the second fiber 227 can equally well function as a first aperture 233.

In addition to the first aperture 233, one or more apertures can be employed to obtain a sharper 3D depth image. A second aperture 235 is preferably positioned between the second lens 215 and the sample 213. In a preferred embodiment, where there is no window 219 and the second lens 215 is convex, the second lens 215 will still be in direct contact with the sample 213 even with the thin second aperture 235 positioned between the sample 213 and the second lens 215.

In the current embodiment of the invention, the second aperture 235 is displayed as a separate element. However, a narrow opening of the optical probe 201 at the point where light is focused out/collected by the second lens 215 can equally well function as a second aperture 235.

A third aperture 237 can preferably be positioned just before the third lens 225 as shown in the current figure. This can further improve the 3D depth image.

The two fibers 203 and 227 are normally arranged such that the direction 239 of the light coming out of the first fiber 203 and the direction 241 of the light entering the second fiber 227 are at an angle of α=90° in relation to one another. Alternative arrangements of the two fibers 203 and 227 and consequently the direction of the light exiting/entering them (239 and 241, respectively) can also be found, yielding an angle α≠90°.

The two fibers 203 and 227 are preferably multi mode fibers, but could also be single mode fibers.

Figure 3:
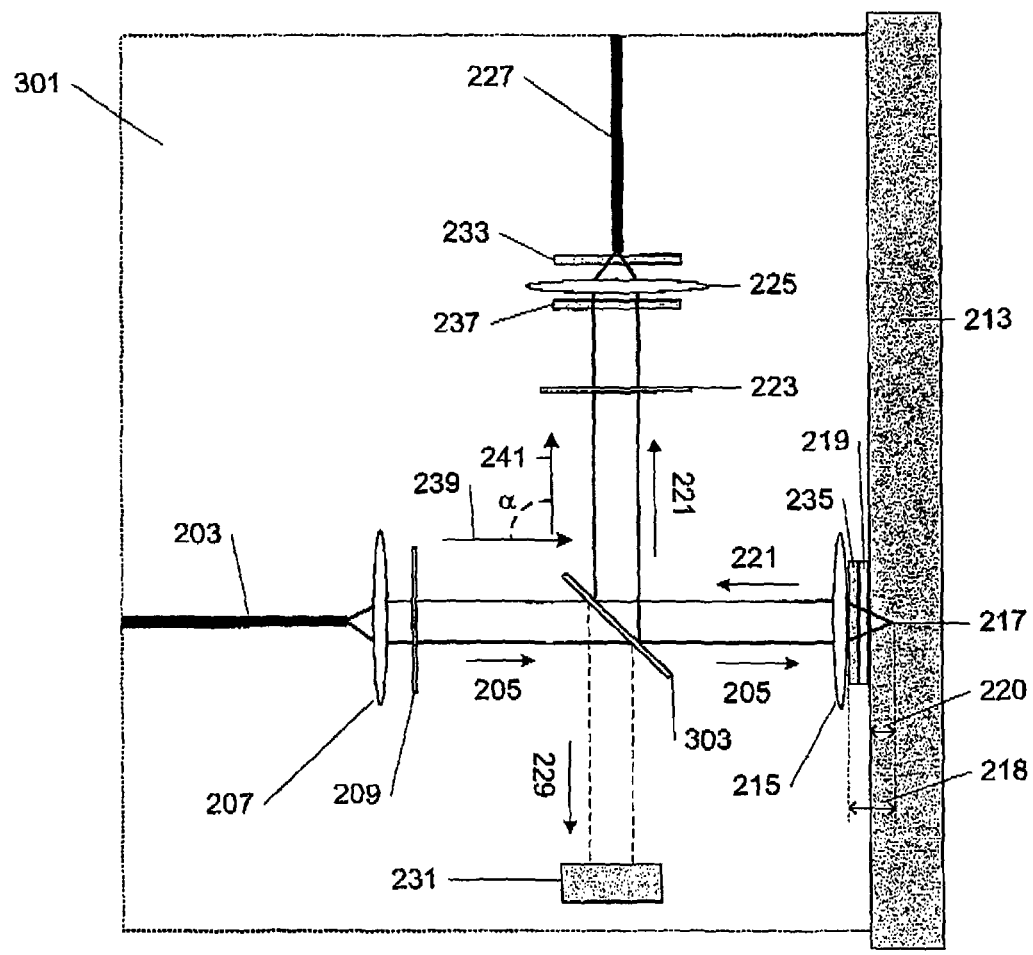
FIG. 3 shows a second embodiment of an optical probe according to the invention.

FIG. 3 shows a second embodiment of the invention, where the optical probe 301 comprises a first optical fiber 203 for guiding light into the optical probe 301, a first lens 207 for collimating the incoming light 205, a first filter 209 blocking any percentage between 0 and 100 of frequencies outside the frequency of the incoming light, a second lens 215 focusing the incoming light 205 into and for collecting the altered light 221 from the sample 213, a second filter 223 for optically filtrating the altered light 221, a third lens 225 for focusing the altered light 221 into a second optical fiber 227, and a light logging device 231, which detects intensity variations in the incoming light.

The two fibers 203 and 227 are preferably multi mode fibers, but could also be single mode fibers. The two fibers 203 and 227 are normally arranged such that the direction 239 of the light exiting the first fiber 203 and the direction 241 of the light entering the second fiber 227 are perpendicular in relation to one another. Alternative arrangements of the two fibers 203 and 227 and consequently the direction of the light exiting/entering them can also be found.

The two filters 209 and 223 are normally band-pass filters, notch filters, edge filters or such. The second lens 215 is preferably convex, but could also be planar.

The optical probe 301 further comprises a dichroic mirror 303 that either reflects or transmits any percentage between 0 and 100 of the light. The dichroic mirror 303 is in the current embodiment positioned at an angle of 45° in relation to the propagating direction of the incoming light 205, but could be positioned at an angle between 0-90° as well.

According to the second embodiment of the invention, the dichroic mirror 303 allows the majority of the incoming light 205 to pass through the dichroic mirror 303 and reflects only a smaller part 229 of the incoming light which is detected by the light logging device 231.

The altered light 221 is reflected by the dichroic mirror 303 at an approximate 90 degree angle.

In one embodiment of the invention, the percent of the incoming light 205 which is reflected and transmitted by the dichroic mirror 303 is re_in ≤30 and tr_in ≥70, respectively, and the percent of the altered light 221 which is reflected and transmitted by the dichroic mirror 303 is re_se≥70 and tr_se≤30, respectively, where re_in+tr$_{13}$ in=100 percent and re$_{13}$ se+tr_se=100 percent.

In another embodiment of the invention, the percent of the incoming light 205 which is reflected and transmitted by the dichroic mirror 303 is re_in ≤10 and tr_in ≥90, respectively, and the percent of the altered light 221 which is reflected and transmitted by the dichroic mirror 303 is re_se≥90 and tr_se≤10, respectively, where re_in+tr_in=100 percent and re_se+tr_se=100 percent.

The optical probe 301 may further optionally comprise a narrow window 219, which is positioned between the second lens 215 and the sample 213, a first optical aperture 233, a second aperture 235 normally positioned between the second lens 215 and the sample 213 and a third aperture 237 normally positioned just before the third lens 225. According to this second embodiment of the invention, the apertures 233 and 235 are displayed as a separate element. However, a narrow opening of the second fiber 227 can equally well function as a first aperture 233, and a narrow opening of the optical probe 301 at the point where light is focused out/collected by the second lens 215 can equally well function as a first aperture 233.

Typical sample penetration depths 220 are in the range between 1/10-3 mm depending on the focal length 218 of the second lens 215 and the thickness of the window 219, if such is part of the optical probe 301. Both shorter and longer penetrations depths 220 can also be obtained.

The advantages with the optical probe 301 are the same as the ones described in relation to the optical probe 201 shown in FIG. 2.

Figure 4:
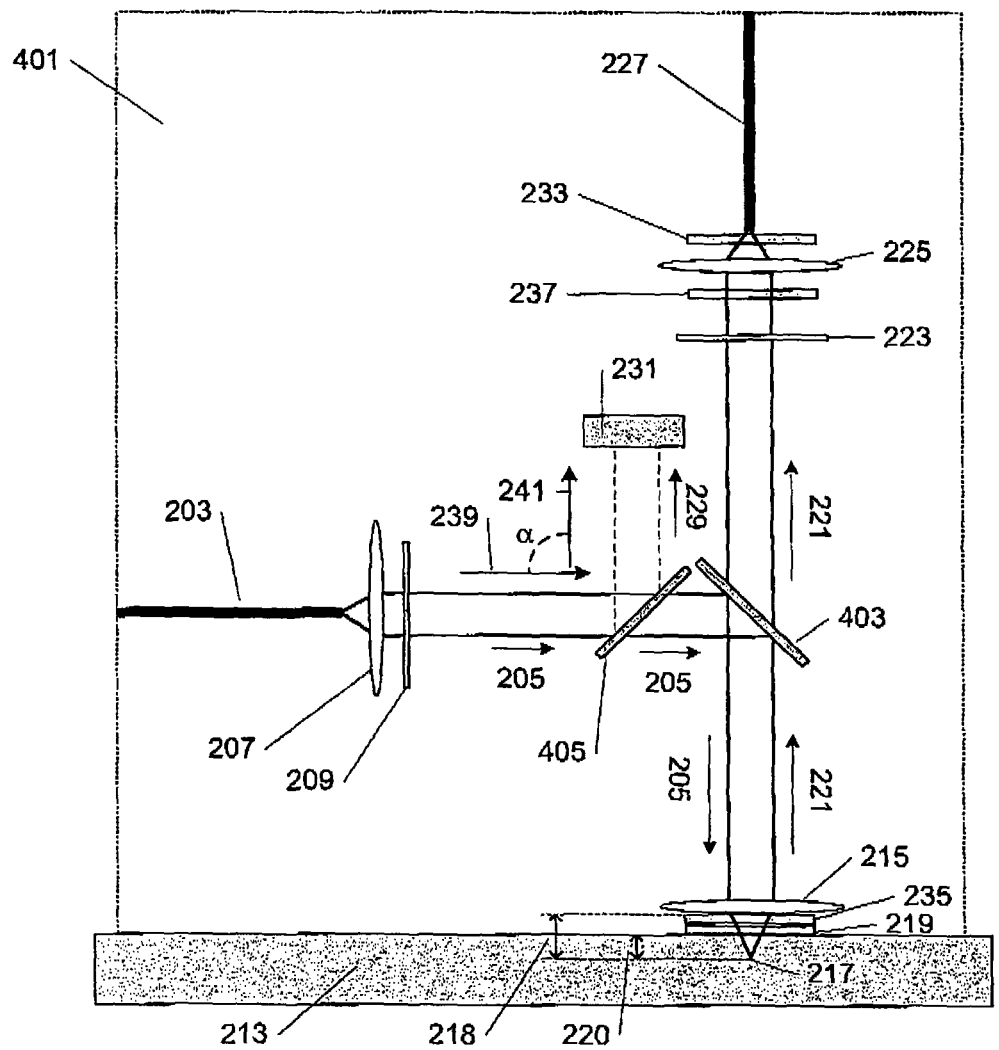
FIG. 4 shows a third embodiment of an optical probe according to the invention.

FIG. 4 shows a third embodiment of the invention, where the optical probe 401 comprises a first optical fiber 203 for guiding light into the optical probe 301, a first lens 207 for collimating the incoming light 205, a first filter 209 blocking any percentage between 0 and 100 of frequencies outside the frequency of the incoming light, a second lens 215 focusing the incoming light 205 into and for collecting the altered light 221 from the sample 213, a second filter 223 for optically filtrating the altered light 221, a third lens 225 for focusing the altered light 221 into a second optical fiber 227 and a light logging device 231, which detects intensity variations in the incoming light.

The two fibers 203 and 227 are preferably multi mode fibers, but could also be single mode fibers. The two fibers 203 and 227 are normally arranged such that the direction 239 of the light coming out of the first fiber 203 and the direction 241 of the light entering the second fiber 227 are perpendicular in relation to one another. Alternative arrangements of the two fibers 203 and 227 and consequently the direction of the light coming out of/entering them can also be found.

The two filters 209 and 223 are normally band-pass filters, notch filters, edge filters or such. The second lens 215 is preferably convex, but could also be planar.

The optical probe 401 further comprises a dichroic mirror 403 that either reflects or transmits any percentage between 0 and 100 of the light. The dichroic mirror 403 is in the current embodiment positioned at an angle of 45° in relation to the propagating direction of the incoming light 205, but could be positioned at an angle between 0-90° as well.

According to the third embodiment of the invention, the dichroic mirror 403 reflects the majority of the incoming light 205 in a 90 degree angle onto the sample 213 and allows for the altered light 221 to be transmitted through the dichroic mirror 403. Alternatively, the dichroic mirror 403 could transmit the majority of the incoming light 205 and reflect the majority of the altered light 221 from the sample 213, whereby the sample 213 and the optical elements (215, 219, and 235) positioned just before the sample 213 would be positioned as depicted in the second embodiment of the optical probe as shown in FIG. 3.

In contrary to the first and the second embodiments, the smaller part 229 of the incoming light, which is used for light logging, is not collected after passing through or being reflected by the dichroic mirror 403. Instead, an optical splitting device 405 positioned between the first filter 209 and the dichroic mirror 403 is employed to direct a smaller fraction 229 of the incoming light onto the light logging device 231. The splitting device 405 can be a beam splitter, a dichroic mirror allowing most of the incoming light to pass through, a low density filter or similar.

The optical probe 401 may further optionally comprise a narrow window 219, which is positioned between the second lens 215 and the sample 213, a first optical aperture 233, a second aperture 235 normally positioned between the second lens 215 and the sample 213 and a third aperture 237 normally positioned just before the third lens 225. According to this second embodiment of the invention, the apertures 233 and 235 are displayed as a separate element. However, a narrow opening of the second fiber 227 can equally well function as a first aperture 233 and a narrow opening of the optical probe 201 at the point where light is focused out/collected by the second lens 215 can equally well function as a first aperture 233.

Typical sample penetration depths 220 are in the range between 1/10-3 mm depending on the focal length 218 of the second lens 215 and the thickness of the window 219, if such is part of the optical probe 401. Both shorter and longer penetrations depths 220 can also be obtained.

The advantages with the optical probe 401 are the same as the ones described in relation to the optical probe 201 shown in FIG. 2.

The optical probes 201, 301, and 401 are all constructed such that the optical elements inside are positioned in very close proximity to one another, and FIG. 2-4 are thus only meant as illustrations and do not show the accurate distances between the different optical elements.

An advantage with placing the optical elements inside the optical probe in as close proximity as possible, is that this feature enhances both the intensity of the incoming light at the sample focus point and the efficiency by which the altered light is collected, since effects from diffraction of the incoming light and/or the altered light are diminished.

REFERENCES

101: Optical probe
103: Light source, e.g. a laser
105: First fiber
107: Sample, i.e. a patient's arm
109: Second fiber 111: Spectrometer
113: Computer
201: Optical probe according to a first embodiment
203: First fiber
205: Incoming light
207: First lens
209: First filter
211: Dichroic mirror
213: Sample
215: Second lens
217: Focus point
218: Focal length of the first lens
219: Window
220: Penetration depth
221: Altered light
223: Second filter
225: Third lens
227: Second fiber
229: Minor part of the incoming light used for light logging
231: Light logging device
233: First aperture
235: Second aperture
237: Third aperture
239: Direction of the light coming out of the first fiber
241: Direction of the light entering the second fiber
301: Optical probe according to a second embodiment
303: Dichroic mirror
401: Optical probe according to a third embodiment
403: Dichroic mirror
405: Optical splitting device

The invention claimed is:

1. An optical probe for measuring light signals comprising:
an optical fiber for guiding incoming light and having a first end for receiving incoming light and a second end for emitting said incoming light,
a dichroic mirror positioned to receive incoming light from the second end of the optical fiber and having optical characteristics to reflect a majority portion of the incoming light towards a sample location and to pass a minority portion of the incoming light through the dichroic mirror or else positioned to receive incoming light from the second end of the optical fiber and having optical characteristics to pass a majority portion of the received light through the dichroic mirror towards a sample location and to reflect a minority portion of the received light,
a lens positioned and arranged to receive said majority portion of the receiving the incoming light from the dichroic mirror and to focus said incoming light towards a sample location and to collect altered light from said sample location,
a light guide configured to guide said altered light to a measuring location,
a detector configured and arranged to log light and positioned and arranged to receive said minor portion of the incoming light from the dichroic mirror and constructed and arranged to measure intensity fluctuations in said incoming light.

2. An optical probe according to claim 1, wherein said lens is arranged at a surface of said optical probe such that said lens is directly contactable with a sample during measuring.

3. An optical probe according to claim 1, wherein said optical probe further comprises a window having an external surface, where said external surface can in use be brought into direct contact with a sample so that the window is positioned between said lens and said sample, and where the thickness of said window is smaller than the focal length of said lens.

4. An optical probe according to claim 1, wherein said dichroic mirror is positioned at an angle of 45 degrees in relation to the propagating direction of said incoming light out of said first optical fiber.

5. An optical probe according to claim 1, wherein said dichroic mirror
reflects re_in percent and transmits tr_in percent of said incoming light, where re_in+tr_in=100 percent,
reflects re_se percent and transmits tr_se percent of said altered light, where re_se+tr_se=100 percent,
wherein-re_in >=90 percent, tr_in <10 percent, re_se<=30 percent, tr_se>70 percent.

6. An optical probe according to claim 5, wherein said detector is positioned to receive a portion of incoming light that has passed through said dichroic mirror, whereby said detector measures intensity fluctuations in said incoming light transmitted through said dichroic mirror.

7. An optical probe according to claim 6, wherein said dichroic mirror
reflects re_in percent and transmits tr_in percent of said incoming light, where re_in+tr_in=100 percent,
reflects re_se percent and transmits tr_se percent of said altered light, where re_se+tr_se=100 percent,
wherein re_in <=10 percent, tr_in >=90 percent, re_se>=70 percent, tr_se<=30 percent.

8. An optical probe according to claim 1, wherein said detector is positioned to receive a portion of incoming light reflected from said dichroic mirror, whereby said detector measures intensity fluctuations in said incoming light reflected by said dichroic mirror.

9. An optical probe according to claim 1, wherein said light guide is a second optical fiber, an angle $\alpha$ between the direction of light out of said optical fiber and the direction of light entering said second optical fiber is $\alpha$=90 degrees.

10. An optical probe according to claim 9, wherein said optical probe further comprises at least a first aperture positioned immediately in front of said second optical fiber where said first aperture only allows altered light from a focus point of said lens to enter said second optical fiber, thereby ensuring a confocal image.

11. An optical probe according to claim 1, wherein said detector includes a photodiode, a CCD detector, or a thermal transistor.

12. An optical probe according to claim 1,
wherein the dichroic mirror is positioned to receive incoming light from the second end of the optical fiber and has optical characteristics to reflect a majority portion of the incoming light towards the sample location and to pass a minority portion of the incoming light through the dichroic mirror,
wherein the dichroic mirror is further positioned to receive altered light from said sample location and to pass a majority portion of said altered light to said measuring location, whereby said dichroic mirror forms part of said light guide.

13. An optical probe according to claim 1,
wherein the dichroic mirror is positioned to receive incoming light from the second end of the optical fiber and has optical characteristics to pass a majority portion of the received light through the dichroic mirror towards the sample location and to reflect a minority portion of the received light, wherein the dichroic mirror is further positioned to receive altered light from said sample location and to reflect a majority portion of said altered light to said measuring location, whereby said dichroic mirror forms part of said light guide.

14. A method for collecting optical signals from a sample comprising:
 illuminating said sample with light from a light source by means of an optical probe according to claim 1,
 collecting altered light from said sample from the light guide of said optical probe,
 measuring intensities of spectral components of said altered light from said sample and correcting said measured intensities to take account of fluctuations in the incoming light measured by the detector.

* * * * *